United States Patent [19]

O'Lenick, Jr. et al.

[11] Patent Number: 5,296,625

[45] Date of Patent: Mar. 22, 1994

[54] SILICONE ALKOXYLATED ESTERS CARBOXYLATES

[75] Inventors: Anthony J. O'Lenick, Jr., Lilburn; Jeff K. Parkinson, Lawrenceville; Robert T. Torbush, Snellville, all of Ga.

[73] Assignee: Siltech Inc., Norcross, Ga.

[21] Appl. No.: 966,434

[22] Filed: Oct. 26, 1992

Related U.S. Application Data

[63] Continuation-in-part of Ser. No. 788,345, Oct. 16, 1991, abandoned.

[51] Int. Cl.$^5$ .................................................. C07F 7/08
[52] U.S. Cl. ................................ 556/437; 556/440; 554/77
[58] Field of Search ............... 556/440, 437; 554/77

[56] References Cited

U.S. PATENT DOCUMENTS

| | | | |
|---|---|---|---|
| 3,458,554 | 7/1969 | Haluska | 556/440 |
| 3,657,305 | 4/1972 | Morehouse | 556/440 X |
| 3,778,458 | 12/1973 | Morehouse | 556/440 |
| 4,331,797 | 5/1982 | Martin | 556/440 X |
| 4,717,498 | 1/1988 | Maxon | 556/437 X |
| 4,777,277 | 10/1988 | Colas et al. | 556/419 |
| 4,937,277 | 6/1990 | O'Lenick | 556/437 X |
| 5,041,593 | 8/1991 | Plueddemann | 556/440 |
| 5,053,290 | 10/1991 | Canivene et al. | 556/437 X |
| 5,136,063 | 8/1992 | O'Lenick | 556/437 X |
| 5,145,977 | 9/1992 | Petroff et al. | 55/437 |
| 5,210,251 | 5/1993 | Ohashi et al. | 556/437 |

*Primary Examiner*—Paul F. Shaver

[57] ABSTRACT

The invention relates to a series of novel silicone alkoxylated esters which contain terminal carboxyl groups. This class of compounds provides unique solubility in many organic solvents as well as very substantive salts of the carboxylic acid when neutralized with base. The compounds of the present invention are prepared by reacting a the hydroxyl group in a silicone polymer with an anhydride.

16 Claims, No Drawings

SILICONE ALKOXYLATED ESTERS CARBOXYLATES

RELATED APPLICATIONS

This application is a continuation in part of copending application Ser. No. 07/788,345 filed Oct. 16, 1991, now abandoned.

BACKGROUND OF THE INVENTION

1. Field of the Invention

The present invention relates to a series of novel silicone alkoxylated esters which have terminal carboxyl groups. These materials provide outstanding lubrication, and softening when applied to a variety of fiber substrates. The compounds of the present invention are prepared by reacting a hydroxyl containing silicone polymer, and an anhydride.

2. Arts and Practices

Silicone compounds have been known to be active at the surface of cellulosic and synthetic fibers as well as paper. They are good nondurable lubricants and are very stable to oxidation, however, their high cost and lack of efficiency at low concentrations as well as low durability have made their acceptance in commercial products quite low.

In addition to their high cost, silicone compounds have little or no solubility in mineral oils, fatty triglycerides and other classical fatty quaternary compounds used for softening. This has resulted in the inability to prepare stable blends for use as a textile fiber treatment.

In many applications, there is a desire for a more fatty soluble softener. The desired molecule should have the desirable softening and antistatic properties of silicone, yet have compatibility with traditional fatty materials and oils. Even though a textile softener which has both the desirable softening and antistatic properties of silicone as well as compatibility with fatty compounds has been a long felt need, it isn't until the compounds of the present invention that such a system has been attained.

U.S. Pat. No. 3,511,699 to Sterman issued May 12, 1970 teaches that epoxy compounds placed in the silicone backbone by hydrosilation can be cured onto certain fibers to give improved substantivity. The substantivity is based upon the reaction of hydroxyl groups on the cellulosic and the epoxy group in the silicone polymer.

U.S. Pat. No. 4,587,320 issued to Swihart discloses that certain carboxy functional products can be prepared by equilibrating silicone glycols and a carboxy silane. The compounds of the Swihart invention because they are prepared by reacting a performed carboxy silane with a silicone glycol do not produce the desired functionality of the present invention. As will become clear from the disclosure the compounds of the present invention are carboxy functional esters of alkoxylated glycols. They are quite different in structure and in function form the Swihart compounds.

THE INVENTION

Object of the Invention

It is the object of the present invention to provide novel silicone ester having a terminal carboxy group present. These compounds are substantive to the surface of a fiber and other textile materials including cellulosic material and have increased solubility in fatty materials including mineral oil, fatty triglycerides and traditional fatty quaternary ammonium compounds. The compounds of the present invention render the lubricity, and hydrophobicity generally seen in silicone compounds, but because they are esterified with fatty groups have greater solubility in hydrocarbon oils as well as fatty materials than the traditional silicone compounds which are insoluble in those materials. The carboxy group can be neutralized with any alkaline materials like amines, hydroxides and other materials.

It is another objective of the current invention to provide silicone ester carboxylates which can be used in personal care, textile, and industrial formulations to render softness and lubrication to the substrates being treated. The superior solubility properties are an important benefit, since this is a major aspect of consumer perception of softness in consumer and industrial laundry applications. Application of the compounds of the invention can be from solvent, aqueous dispersion or solution, or applied neat in these processes.

Summary of the Invention

The present invention relates to novel silicone alkoxylated esters which contain carboxyl groups. The compounds by virtue of the fatty ester group are soluble in fatty and hydrocarbon products, but have many of the functional softening and lubrication properties of silicone. The solubility of these materials can be altered by simple pH adjustment. In the acid form these materials are silicone like it their solubility parameters. At higher pH values they become soluble in fatty materials and mineral oils. This property makes these materials excellent additives for highly effective surface modifying finishes for fiber and textiles. The compounds of the present invention are substantive to cellulosic and synthetic fibers as well as metal surfaces and plastic polymers.

As will become clear from the disclosure, the compounds of the present invention while having silicone present in the molecule, have unique solubility in organic materials like triglycerides, mineral oil and the like. This property is a direct result of the structure. The pendant group needs to contain (a) a silicone atom linked covalently through carbon to (b) an alkoxylated portion linked covalently to (c) an ester function, linked covalently to (d) an R" linking group containing carbon atoms linked covalently to (E) a COOH group. Compounds lacking these functional parts do not give the desired solubilization properties. Optionally the carboxyl group can be neutralized with base or an amine to give an ionic compound.

The compounds of the present invention therefore have a pendant group which is as follows:

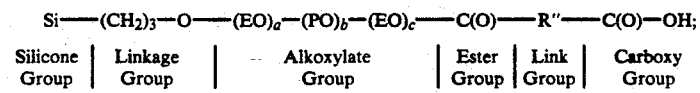

$$\text{Si}-(CH_2)_3-O-(EO)_a-(PO)_b-(EO)_c-C(O)-R''-C(O)-OH;$$

| Silicone Group | Linkage Group | Alkoxylate Group | Ester Group | Link Group | Carboxy Group |

The Silicone Group is soluble in silicone materials; the alkoxylate group renders water solubility to the molecule; the ester linkage taken with the carbon linkage group make up the oil soluble group and the terminal group is the ionizable group.

These materials will allow for the solubilization of water, fatty oils and silicone oils into one phase. Standard fatty surface active agents or surfactants have only water soluble portion and an oil soluble portion. An example is a stearyl alcohol ethoxylate.

Fatty Portion | Water Soluble Portion

This type of material will allow for solubilization of fatty oils and water, but not silicones.

Silicone copolyols, on the other hand have a silicone soluble portion and a water soluble portion. These materials allow for the solubilization of silicone and water, but not in the presence of fatty oils.

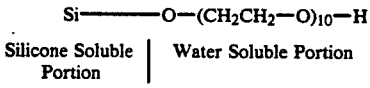

Silicone Soluble Portion | Water Soluble Portion

There are many instances were there is a desire to solubilize water, fatty oils and silicone into a single system. Each component is mutually insoluble in each other. Any two of the three can be solubilized by addition of surface active agent, either conventional fatty surfactants or silicone surfactants. But conventional surfactants and silicone surfactants do not allow for the preparation of solubilized products which contain all three, only the compounds of the present invention work for all three.

The carboxy silicones of the prior art (U.S. Pat. No. 4,587,320) which lack the above mentioned groups, do not perform the solubilization properties that the compounds of the present invention perform.

The compounds of the present invention are prepared by the reaction of an anhydride with an hydroxy silicone polymer. Suitable anhydrides for the preparation of the compounds of the present invention are cyclic anhydrides, which react easily at mild conditions with the silicone hydroxyl group to produce an ester carboxylate. Typical of the reaction is the following sequence utilizing succinic anhydride;

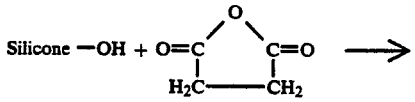

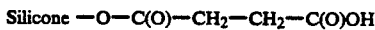

Silicone —O—C(O)—CH$_2$—CH$_2$—C(O)OH

The silicone—OH represents the hydroxyl group on the silicone polymer described elsewhere in the disclosure.

The compounds of this invention are silicone ester carboxylates made by the reaction of an anhydride and a hydroxy containing silicone compound. The compounds of the present invention conform to the following structure;

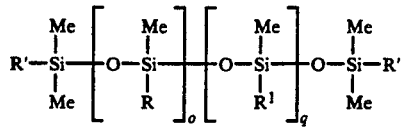

wherein;
Me is methyl;
R and R' are CH$_3$ or

—(CH$_2$)$_3$—O—(EO)$_a$—(PO)$_b$—(EO)$_c$—C(O)—R"—C(O)—OH;

with the proviso that both R and R' are not CH$_3$;
R" is selected from —CH$_2$——CH$_2$—; —CH=CH—; —CH$_2$—C(R$^7$)—H;

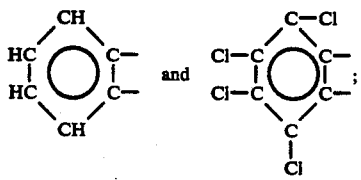

R$^7$ is alkyl having from 1 to 20 carbon atoms;
R$^1$ is selected from lower alkyl CH$_3$(CH)$_n$— or phenyl;
n is an integer from 0 to 8;
a, b and c are integers independently ranging from 0 to 20;
EO is an ethylene oxide residue —(CH$_2$CH$_2$—O)—;
PO is a propylene oxide residue —(CH$_2$CH(CH$_3$)—O)—;
o is an integer ranging from 1 to 100;
q is an integer ranging from 0 to 500.

PREFERRED EMBODIMENTS

In a preferred embodiment, a+b+c is greater than zero. This proviso requires that the silicone be alkoxylated and results in improved solubilization properties for the silicone in oils.

In another preferred embodiment, the R" is —CH$_2$—CH$_2$—.

In still another embodiment R" is —CH=CH—.

In another preferred embodiment R" is —CH$_2$—C(R$^7$)—H.

In still another preferred embodiment R" is

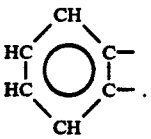

In still another preferred embodiment R" is

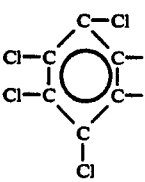

In still another preferred embodiment $R^7$ is alkyl having from 6 to 20 carbon atoms.

In a more preferred embodiment $R^7$ is alkyl having from 12 to 20 carbon atoms.

EXAMPLES

The compounds of the present invention are prepared by the reaction of a hydroxy silicone compound and an anhydride. Examples of suitable reactants are as follows;

REACTANTS

Anhydrides

The various anhydrides listed are all items of commerce and are prepared by methods known to those skilled in the art.

Reactant Example I (Succinic Anhydride)

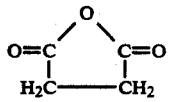

Reactant Example II (Alkyl Succinic Anhydride)

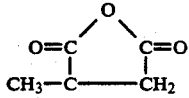

Reactant Example III (Alkyl Succinic Anhydride)

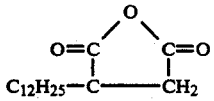

Reactant Example IV (Alkyl Succinic Anhydride)

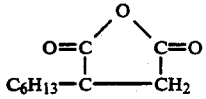

Reactant Example V (Alkyl Succinic Anhydride)

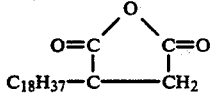

Reactant Example VI (Alkyl Succinic Anhydride)

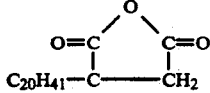

Reactant Example VII (Maleic Anhydride)

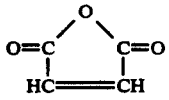

Reactant Example VIII (Phthalic Anhydride)

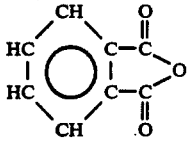

Reactant Example IX (Tetrachlorophthalic anhydride)

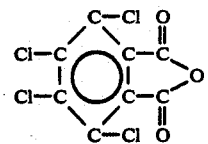

Hydroxy Silicone Compounds

Many manufacturers offer a series of hydroxy silicone compounds suitable for use as raw materials in the preparation of the esters of the present invention. These materials are marketed under the many trade names. Siltech Inc, Union Carbide, Dow Corning, Mazer and many other manufacturers also offer the compounds commercially.

The preferred method of placing this type of reactive hydroxyl group into the silicone polymer is by the reaction of silanic hydrogen containing polymer with allyl alcohol alkoxylates. This technology is well known to those skilled in the art and are described in U.S. Pat. No. 4,083,856. These hydroxyl functional silicone compounds are subsequently reacted with anhydrides, to make the compounds of the present invention.

Additionally, hydroxy silicone compounds are available from Siltech Inc. Norcross Ga. These compounds conform to the following generic structure:

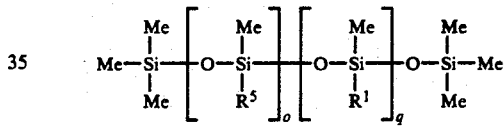

wherein;

Me is methyl;

$R^5$ is $-(CH_2)_3-O-(EO)_a-(PO)_b-(EO)_c-H$ $R^1$ is selected from lower alkyl $CH_3(CH)_n-$ or phenyl;

n is an integer from 0 to 8;

a, b and c are integers independently ranging from 0 to 20;

EO is an ethylene oxide residue $-(CH_2CH_2-O)-$;

PO is a propylene oxide residue $-(CH_2CH(CH_3)-O)-$;

o is an integer ranging from 1 to 100;

q is an integer ranging from 0 to 500.

| Example | Name | a | b | c | o | q |
|---|---|---|---|---|---|---|
| 1 | Siltech H 1000 | 3 | 0 | 0 | 2 | 54 |
| 2 | Siltech H 1100 | 10 | 5 | 10 | 10 | 100 |
| 3 | Siltech H 1200 | 20 | 20 | 20 | 2 | 56 |
| 4 | Siltech H 1300 | 10 | 10 | 10 | 6 | 26 |
| 5 | Siltech H 1400 | 0 | 10 | 0 | 4 | 200 |
| 6 | Siltech H 1500 | 5 | 5 | 5 | 2 | 50 |
| 7 | Siltech H 1600 | 0 | 6 | 0 | 10 | 25 |
| 8 | Siltech H 1700 | 0 | 0 | 0 | 5 | 10 |

Terminal Substituted Dimethicone Copolyol Compounds

Terminal substituted dimethicone copolyol compounds are well known and are marketed in the trade under many names.

The preferred method of placing this type of reactive hydroxyl group into the silicone polymer is by the reaction of terminal silanic hydrogen containing polymer with allyl alcohol alkoxylates. This technology is well known to those skilled in the art and are described in U.S. Pat. No. 4,083,856.

These materials are available from Siltech Inc. Norcross Ga. and are marketed under the Siltech T series trade name.

$$R^6-\underset{\underset{Me}{|}}{\overset{\overset{Me}{|}}{Si}}-\left[O-\underset{\underset{Me}{|}}{\overset{\overset{Me}{|}}{Si}}\right]_o-\left[O-\underset{\underset{R^1}{|}}{\overset{\overset{Me}{|}}{Si}}\right]_q-O-\underset{\underset{Me}{|}}{\overset{\overset{Me}{|}}{Si}}-R^6$$

wherein;
Me is methyl;
$R^6$ is $-(CH_2)_3-O-(EO)_a-(PO)_b-(EO)_c-H$
$R^1$ is selected from lower alkyl $CH_3(CH)_n-$ or phenyl;
n is an integer from 0 to 8;
a, b and c are integers independently ranging from 0 to 20;
EO is an ethylene oxide residue $-(CH_2CH_2-O)-$;
PO is a propylene oxide residue $-(CH_2CH(CH_3)-O)-$;
o is an integer ranging from 1 to 100;
q is an integer ranging from 0 to 500.

| Example | Name | a | b | c | Equivalent Molecular Weight |
|---|---|---|---|---|---|
| 9 | Siltech T 701 | 0 | 0 | 0 | 1,000 |
| 10 | Siltech T 706 | 5 | 1 | 0 | 6,000 |
| 11 | Siltech T 710 | 2 | 1 | 1 | 10,000 |
| 12 | Siltech T 750 | 10 | 5 | 10 | 50,000 |
| 13 | Siltech T 790 | 20 | 20 | 20 | 86,000 |

General Reaction Conditions

The reaction can be run with either a stoichiometric amount of the anhydride, or an excess of silicone polymer.

Into a suitable round bottom, three neck flask equipped with a thermometer and a nitrogen sparge is added the specified number of grams of the specified silicone compound and the specified number of grams of the specified anhydride. The reaction mass is blanketed with nitrogen, and heated to 80 and 110 C. under the inert nitrogen blanket. Within four to five hours the theoretical acid value is obtained. The product is a clear liquid and is used without additional purification.

EXAMPLE 14

Into a suitable round bottom, three neck flask equipped with a thermometer and a nitrogen sparge is added number 100.0 grams of silicone example 1 and the 1,000.0 grams of succinic anhydride. The reaction mass is then blanketed with nitrogen and heated to 80 and 110 C. This temperature is maintained for four to five hours. The theoretical acid value is obtained. The product is a clear liquid and is used without additional purification.

EXAMPLES 15-32

Example 14 is repeated only this time substituting the specified number of grams of the anhydride specified and the specified type and number of grams of silicone compound as shown below:

| Example | Anhydride Reactant Example | Grams | Silicone Compound Example | Grams |
|---|---|---|---|---|
| 15 | I | 100.0 | 1 | 2,329.0 |
| 16 | II | 115.0 | 2 | 2,032.0 |
| 17 | III | 269.0 | 3 | 5,129.0 |
| 18 | IV | 185.0 | 4 | 347.6 |
| 19 | V | 316.0 | 5 | 4,407.0 |
| 20 | VI | 340.0 | 6 | 2,743.0 |
| 21 | VII | 98.0 | 7 | 3,550.8 |
| 22 | VIII | 148.0 | 8 | 1,512.4 |
| 23 | IX | 288.0 | 9 | 1,000.0 |
| 24 | I | 100.0 | 10 | 6,000.0 |
| 25 | II | 115.0 | 11 | 10,000.0 |
| 26 | III | 269.0 | 12 | 50,000.0 |
| 27 | IV | 185.0 | 13 | 86,000.0 |
| 28 | V | 316.0 | 1 | 2,329.0 |
| 29 | VI | 340.0 | 2 | 2,032.0 |
| 30 | VII | 98.0 | 3 | 5,129.0 |
| 31 | VIII | 148.0 | 4 | 347.6 |
| 32 | IX | 288.0 | 5 | 4,407.0 | solubilization

The compounds of the present invention were evaluated for their ability to solubilize water, mineral oil and silicone oil. The formulation tested was;

| TEST FORMULATION | |
|---|---|
| Material | % by Weight |
| Water | 85.0 |
| Poly dimethyl siloxane | 5.0 |
| Mineral oil | 5.0 |
| Test Compound | 5.0 |
| Total | 100.0 |

The pH was adjusted to 7.0 with NaOH. The resulting composition was evaluated for stability. The rating used was 1-5 (1 being the worst (split); 5 being the most stable).

| Material Tested | Rating |
|---|---|
| Nonylphenol 9 moles of ethylene oxide (Commercial Source: Olin Chemical) | 2 |
| Silwet 7402 (a silicone copolyol (Commercial Source: Union Carbide) | 1 |
| Tridecyl alcohol 8 moles ethylene oxide (Commercial Source: Alkaril Chemical) | 2 |
| Example 15 (Compound of this invention) | 4 |
| Example 20 (Compound of this invention) | 4 |
| Example 30 (Compound of this invention) | 5 |

As can be clearly seen the compounds of the present invention allow for the preparation of compositions with outstanding stability.

What is claimed:

1. A silicone compound conforming to the following structure;

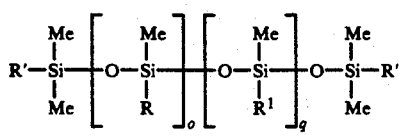

wherein;
Me is methyl;
R and R' are selected from methyl and

—(CH$_2$)$_3$—O—(EO)$_a$—(PO)$_b$—(EO)$_c$—C(O)—R'—C(O)—OH;

with the proviso that both R and R' are not methyl;
R" is selected from —CH$_2$—CH$_2$—; —CH$_2$—C(R$^7$)—H;

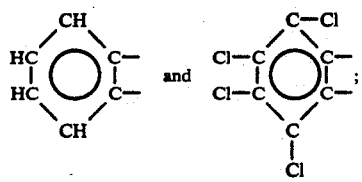

R$^7$ is alkyl having from 1 to 20 carbon atoms;
R$^1$ is selected from lower alkyl CH$_3$(CH)$_n$— or phenyl;
n is an integer from 0 to 8;
a, b and c are integers independently ranging from 0 to 20;
EO is an ethylene oxide residue —(CH$_2$CH$_2$—O)—;
PO is a propylene oxide residue —(CH$_2$CH(CH$_3$)—O)—;
o is an integer ranging from 1 to 100;
q is an integer ranging from 0 to 500.

2. A compound of claim 1 wherein R" is —CH$_2$—CH$_2$—.

3. A compound of claim 1 wherein R" is —CH$_2$—C(R$^7$)—H.

4. A compound of claim 1 wherein R" is

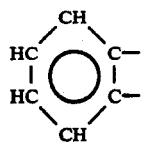

5. A compound of claim 1 wherein R" is

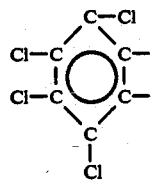

6. A compound of claim 3 wherein R$^7$ is alkyl having from 6 to 20 carbon atoms.

7. A compound of claim 3 wherein R$^7$ is alkyl having from 12 to 20 carbon atoms.

8. A compound of claim 1 wherein R' is methyl.

9. A compound of claim 1 wherein R' is

—(CH$_2$)$_3$—O—(EO)$_a$—(PO)$_b$—(EO)$_c$—C(O)—R'—C(O)—OH.

10. A compound of claim 3 wherein R' is

—(CH$_2$)$_3$—O—(EO)$_a$—(PO)$_b$—(EO)$_c$—C(O)—R'—C(O)—OH.

11. A compound of claim 2 wherein R' is

—(CH$_2$)$_3$—O—(EO)$_a$—(PO)$_b$—(EO)$_c$—C(O)—R'—C(O)—OH.

12. A compound of claim 4 wherein R' is

—(CH$_2$)$_3$—O—(EO)$_a$—(PO)$_b$—(EO)$_c$—C(O)—R'—C(O)—OH.

13. A compound of claim 1 wherein R is

—(CH$_2$)$_3$—O—(EO)$_a$—(PO)$_b$—(EO)$_c$—C(O)—R'—C(O)—OH.

14. A compound of claim 3 wherein R is

—(CH$_2$)$_3$—O—(EO)$_a$—(PO)$_b$—(EO)$_c$—C(O)—R'—C(O)—OH.

15. A compound of claim 5 wherein R is

—(CH$_2$)$_3$—O—(EO)$_a$—(PO)$_b$—(EO)$_c$—C(O)—R'—C(O)—OH.

16. A compound of claim 4 wherein R is

—(CH$_2$)$_3$—O—(EO)$_a$—(PO)$_b$—(EO)$_c$—C(O)—R'—C(O)—OH.

* * * * *

(12) EX PARTE REEXAMINATION CERTIFICATE (5667th)
United States Patent
O'Lenick, Jr. et al.

(10) Number: US 5,296,625 C1
(45) Certificate Issued: Feb. 6, 2007

(54) SILICONE ALKOXYLATED ESTERS CARBOXYLATES

(75) Inventors: Anthony J. O'Lenick, Jr., Lilburn, GA (US); Jeff K. Parkinson, Lawrenceville, GA (US); Robert T. Torbush, Snellville, GA (US)

(73) Assignee: Lambent Technologies, Inc., Norcross, GA (US)

Reexamination Request:
No. 90/006,835, Oct. 29, 2003

Reexamination Certificate for:
Patent No.: 5,296,625
Issued: Mar. 22, 1994
Appl. No.: 07/966,434
Filed: Oct. 26, 1992

Related U.S. Application Data

(63) Continuation-in-part of application No. 07/788,345, filed on Nov. 6, 1991, now abandoned.

(51) Int. Cl.
*C07F 7/08* (2006.01)

(52) U.S. Cl. .......................... 556/437; 556/440; 554/77
(58) Field of Classification Search ................. 556/437, 556/440; 554/77
See application file for complete search history.

(56) References Cited

U.S. PATENT DOCUMENTS 3,560,544 A   2/1971   Halnska

*Primary Examiner*—Samuel Barts

(57) ABSTRACT

The invention relates to a series of novel silicone alkoxylated esters which contain terminal carboxyl groups. This class of compounds provides unique solubility in many organic solvents as well as very substantive salts of the carboxylic acid when neutralized with base. The compounds of the present invention are prepared by reacting a the hydroxyl group in a silicone polymer with an anhydride.

EX PARTE REEXAMINATION CERTIFICATE ISSUED UNDER 35 U.S.C. 307

THE PATENT IS HEREBY AMENDED AS INDICATED BELOW.

AS A RESULT OF REEXAMINATION, IT HAS BEEN DETERMINED THAT:

Claims 1–16 are cancelled.

* * * * *